(12) United States Patent
Huang et al.

(10) Patent No.: US 12,201,316 B2
(45) Date of Patent: Jan. 21, 2025

(54) MICRO NEEDLE HOLDER CAPABLE OF CUTTING SUTURES

(71) Applicants: Hui-Fu Huang, Yuanlin (TW); Shiuan-Tang Chang, Mountain View, CA (US)

(72) Inventors: Hui-Fu Huang, Yuanlin (TW); Shiuan-Tang Chang, Mountain View, CA (US)

( * ) Notice: Subject to any disclaimer, the term of this patent is extended or adjusted under 35 U.S.C. 154(b) by 99 days.

(21) Appl. No.: 17/850,142

(22) Filed: Jun. 27, 2022

(65) Prior Publication Data
US 2022/0409228 A1    Dec. 29, 2022

(30) Foreign Application Priority Data
Jun. 28, 2021  (TW) .................................. 110123632

(51) Int. Cl.
*A61B 17/30*    (2006.01)
*A61B 17/04*    (2006.01)

(52) U.S. Cl.
CPC .......... *A61B 17/30* (2013.01); *A61B 17/0467* (2013.01); *A61B 17/0483* (2013.01); *A61B 2017/305* (2013.01)

(58) Field of Classification Search
CPC . A61B 17/30; A61B 17/0467; A61B 17/0483; A61B 17/062; A61B 17/3201; A61B 17/3213; A61B 2017/301; A61B 2017/303; A61B 2017/305; A61B 2017/00353
See application file for complete search history.

(56) References Cited

U.S. PATENT DOCUMENTS

| | | | | |
|---|---|---|---|---|
| 1,837,277 A * | 12/1931 | Lund | ...................... | A61B 17/26 606/210 |
| 4,165,745 A * | 8/1979 | Heifetz | .............. | A61B 17/2804 606/147 |
| 4,825,864 A * | 5/1989 | Hariri | ..................... | A61B 17/30 606/1 |
| 4,949,717 A * | 8/1990 | Shaw | ................... | A61B 17/062 606/174 |
| 5,065,516 A * | 11/1991 | Dulebohn | .............. | B26B 13/28 606/208 |

\* cited by examiner

*Primary Examiner* — Katherine H Schwiker
(74) *Attorney, Agent, or Firm* — Sughrue Mion, PLLC

(57) ABSTRACT

A micro needle holder capable of cutting sutures, configured for holding needles and cutting sutures during microsurgeries, includes a needle holding unit and a suture cutting unit. The needle holding unit includes a pair of first plier bodies and a first shaft, where each of the first plier bodies has a needle holding end, a first shaft connecting part, and a first plier arm. The suture cutting unit includes a pair of second plier bodies and a second shaft, where each of the second plier bodies includes a suture cutting end, a second shaft connecting part, and a second plier arm. Moreover, the first plier arms are respectively connected with the second plier arms and are configured to elastically open and close corporately.

7 Claims, 3 Drawing Sheets

MICRO NEEDLE HOLDER CAPABLE OF CUTTING SUTURES

TECHNICAL FIELD OF THE INVENTION

The present disclosure relates to an instrument for microsurgery, and more particularly to a micro needle holder capable of cutting sutures.

DESCRIPTION OF RELATED ART

Microsurgeries refers to the handling of vessels or nerves, such as engagement between small vessels, small nerves, lymph, or small tube-like structures, under a microscope.

During operation of a microsurgery, a clinician must clamp a tiny tissue to be stitched by one hand using micro forceps, and hold a needle by the other hand using a micro needle holder, thereby to carry the needle and lead a suture during stitching of the tiny tissue. When the clinician completes making a tie of the stitching and needs to cut the suture, someone must assist in delivering the micro scissors to swap the micro needle holder due to the clinician's eyes must focus on the images of a microscope, so that the clinician can use the micro scissors to cut the suture. In other words, the clinician must be assisted by an assistant nearby when performing microsurgeries, which is considerably inconvenient for the clinician as the necessary to call and wait for the assistant to swap the micro needle holder for the micro scissors during each cutting of the suture.

SUMMARY OF THE INVENTION

Therefore, an objective of this disclosure is to provide a micro needle holder capable of cutting sutures that can solve the aforementioned problems.

As such, according to some embodiments disclosed herein, the micro needle holder capable of cutting sutures of this disclosure is configured for holding needles and cutting sutures during microsurgeries, where the micro needle holder capable of cutting sutures comprises: a needle holding unit and a suture cutting unit. The needle holding unit comprises a pair of first plier bodies and a first shaft, where each of the first plier bodies has a needle holding end, a first shaft connecting part in connection with the needle holding end, and a first plier arm in connection with the first shaft connecting part, the pair of first plier bodies are over-stacked via the first shaft connecting parts and in an intersecting configuration, the first shaft pivoted at the first shaft connecting parts, so that the first shaft connecting parts are rotatably connected relative to each other, the needle holding ends are configured to open and close relative to each other, and the first plier arms are configured to open and close relative to each other. The suture cutting unit comprises a pair of second plier bodies and a second shaft, where each of the second plier bodies has a suture cutting end, a second shaft connecting part in connection with the suture cutting end, and a second plier arm in connection with the second shaft connecting part, the pair of second plier bodies are over-stacked via the second shaft connecting parts and in an intersecting configuration, the second shaft pivoted at the second shaft connecting parts, so that the second shaft connecting parts are rotatably connected relative to each other, the suture cutting ends are configured to open and close relative to each other, and the second plier arms are configured to open and close relative to each other. In further embodiments, the first plier arms are respectively connected with the second plier arms, and the first plier arms and the second plier arms can elastically open and close corporately.

In some embodiments, distal ends of the first plier arms are movably connected to distal ends of the second plier arms respectively, and at least one of the needle holding unit and the suture cutting unit further comprises an elastic member provided between the first plier arms or the second plier arms, so that the first plier arms and the second plier arms are elastically opened and closed.

In some embodiments, the distal ends of the first plier arms are pivoted with the distal ends of the second plier arms respectively.

In some embodiments, each of the first plier arms and the second plier arms comprises an elastic section at the distal ends thereof, and the elastic sections of the first plier arms are respectively connected with the elastic sections of the second plier arms.

In some embodiments, the first plier arms and the second plier arms are made of a material selected from any one of titanium alloy, tantalum alloy, copper alloy, aluminum alloy, magnesium alloy, stainless steel, nickel alloy and silicone rubber.

In some embodiments, an opening angle between the suture cutting ends is between 5 to 30 degrees.

In some embodiments, the suture cutting ends have a curved shape bent in a direction from one end connected to the second shaft connecting parts toward a distal end.

In some embodiments, an opening angle between the needle holding ends is between 5 to 30 degrees.

In some embodiments, the needle holding ends have a curved shape bent in a direction from one end connected to the first shaft connecting parts toward a distal end.

The present disclosure provides the following technical effects: the needle holding ends and the suture cutting ends disposed on opposite sides may enable an user to operate single-handily to select the needle holding ends for holding the needle or select the suture cutting ends for cutting off the suture, the stitching movement and suture cutting movement may be accomplished in one iteration, the inconvenience during procedure of microsurgeries may be reduced, and any possible mishaps while waiting for exchange of tools may be avoided.

BRIEF DESCRIPTION OF THE DRAWINGS

Other features and effects of this disclosure will be clearly presented in the embodiments with reference to the drawings, where.

DETAILED DESCRIPTION OF THE INVENTION

Before the present disclosure is described in detail, it should be noted that similar components in the following description will be indicated in a same numeral.

Figure 1:
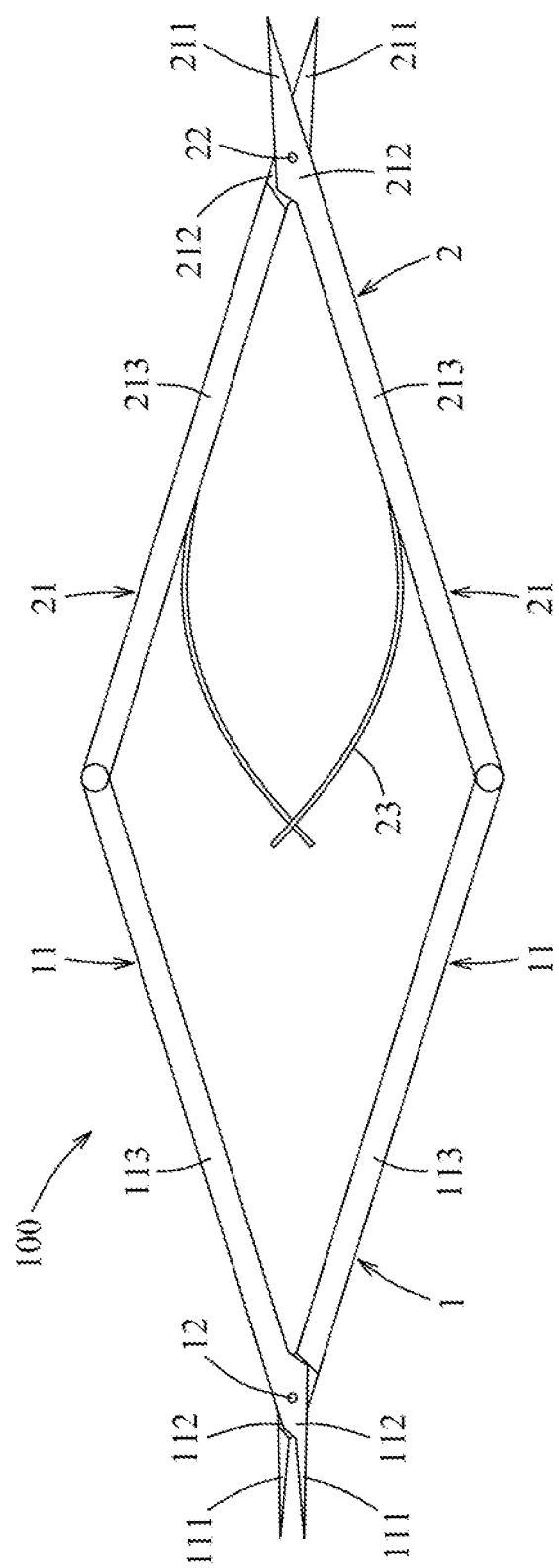
FIG. 1 is a schematic diagram illustrating a first embodiment of the micro needle holder capable of cutting sutures of the present disclosure.

Referring to FIG. 1, a first embodiment of the micro needle holder capable of cutting sutures of the present disclosure is configured for holding needles and cutting sutures during microsurgeries, the micro needle holder capable of cutting sutures 100 comprises a needle holding unit 1 and a suture cutting unit 2.

The needle holding unit 1 comprises a pair of first plier bodies 11 and a first shaft 12, where each of the first plier bodies 11 has a needle holding end 111, a first shaft connecting part 112 in connection with the needle holding end 111, and a first plier arm 113 in connection with the first shaft connecting part 112, the pair of the first plier bodies 11 are over-stacked via the first shaft connecting parts 112 and in an intersecting configuration, the first shaft 12 is pivoted at the first shaft connecting parts 112, so that the first shaft connecting parts 112 may be rotatably connected relative to each other, the needle holding ends 111 may be opened and closed relative to each other, and the first plier arms 113 may be opened and closed relative to each other.

The suture cutting unit 2 comprises a pair of second plier bodies 21 and a second shaft 22, where each of the second plier bodies 21 has a suture cutting end 211, a second shaft connecting part 212 in connection with the suture cutting end 211, and a second plier arm 213 in connection with the second shaft connecting part 212, the pair of the second plier bodies 21 are over-stacked via the second shaft connecting parts 212 and in an intersecting configuration, the second shaft 22 is pivoted at the second shaft connecting parts 212, so that the second shaft connecting parts 212 may be rotatably connected relative to each other, the suture cutting ends 211 may be opened and closed relative to each other, and the second plier arms 213 may be opened and closed relative to each other.

In some embodiments, the first plier arms 113 are respectively connected with the second plier arms 213 and may be elastically opened and closed corporately. In this first embodiment, distal ends of the first plier arms 113 are pivoted on distal ends of the second plier arms 213 respectively, and the suture cutting unit 2 further comprises an elastic member 23 provided between the second plier arms 213, so that the first plier arms 113 and the second plier arms 213 can be elastically opened and closed. In a varied embodiment, the needle holding unit 1 may further comprises an elastic member 23 provided between the first plier arms 113, so that the first plier arms 113 and the second plier arms 213 can be elastically opened and closed; alternatively, the needle holding unit 1 and the suture cutting unit 2 may each comprises an elastic member 23 provided between the first plier arms 113 and between the second plier arms 213, respectively.

The elastic member 23 keeps the first plier arms 113 and the second plier arms 213 relatively open during an unemployed state, and keeps the needle holding ends 111 and the suture cutting ends 211 relatively open at the same time. When a user applies force on the first plier arms 113 or the second plier arms 213 to make the first plier arms 113 and the second plier arms 213 approach each other, the needle holding ends 111 are made to abut against each other to hold the needle, and the suture cutting ends 211 are made to abut against each other to cut off the suture. When the user removes the force, the first plier arms 113 and the second plier arms 213 are restored to the relatively open state by the elastic member 23. Since the diameters of the needles and sutures used in general microsurgeries are about 0.02 to 0.04 mm, the sizes of the needle holding ends 111 and the suture cutting ends 211 are rather small, and the needle holding ends 111 and the suture cutting ends 211 are kept open by elastic force, which can facilitate the operation. Preferably, an opening angle held for the needle holding ends 111 and the suture cutting ends 211 is between 5 to 30 degrees. In this embodiment, the first plier bodies 11 and the second plier bodies 21 are made of stainless steel, which can withstand high temperature sterilization and collision, and other suitable materials can also be selected from titanium alloy, tantalum alloy, copper alloy, aluminum alloy, magnesium alloy, nickel alloy, or silicone rubber, etc.

During holding of a needle, the user may hold the first plier bodies 113 in hand and apply force thereto, so as to hold the needle by the needle holding ends 111. During cutting of a suture, the user merely needs to switch direction of the needle holding unit 1 and the suture cutting unit 2, making the suture cutting ends 211 facing the suture, hold the second plier bodies 213 in hand and apply force thereto, so as to cut the suture by the suture cutting ends 211. As such, the user may single-handily operate and switch direction of the needle holding unit 1 and the suture cutting unit 2 without help from others, and the cutting of the suture may be operated by the suture cutting unit 2 upon completion of the stitching process. Accordingly, the stitching movement and suture cutting movement may be accomplished in one iteration, the inconvenience during procedure of microsurgeries may be reduced, and any possible mishaps while waiting for exchange of tools may be avoided.

Figure 2:
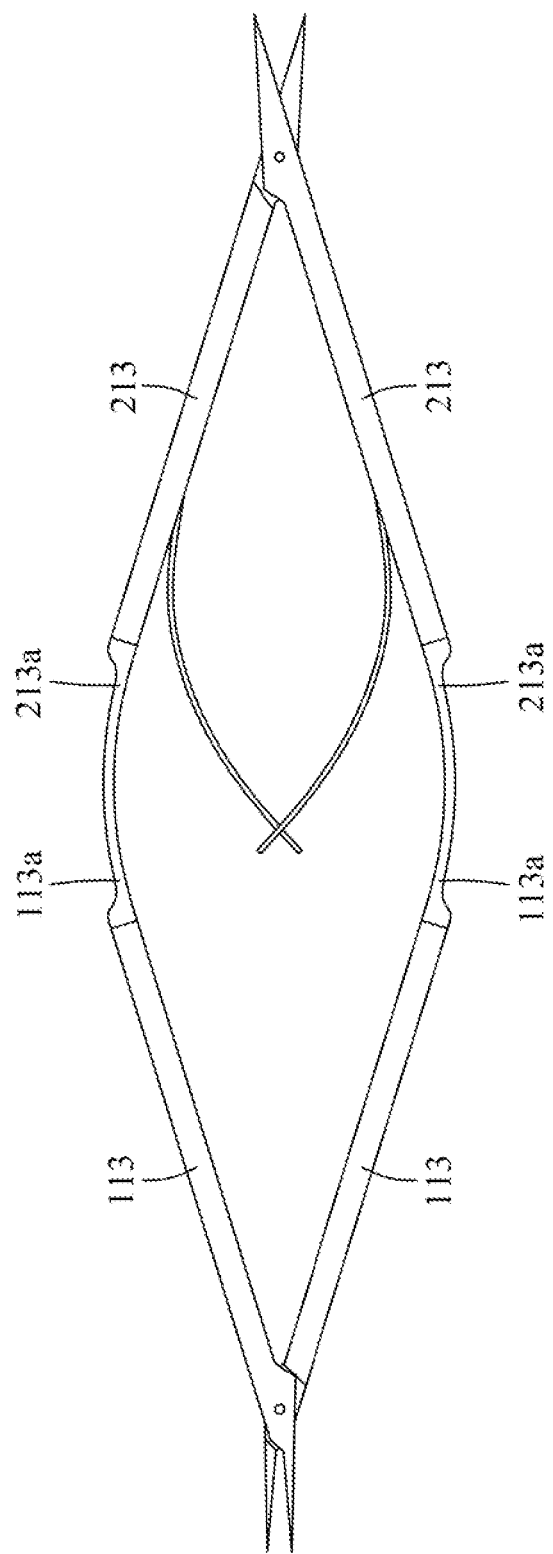
FIG. 2 is a schematic diagram illustrating a second embodiment of the micro needle holder capable of cutting sutures of the present disclosure.

Referring to FIG. 2, a second embodiment of the micro needle holder capable of cutting sutures of the present disclosure is substantially the same as the first embodiment, and differences lies in that, in the second embodiment, each of the first plier arms 113 and the second plier arms 213 comprises an elastic section 113a and an elastic section 213a, respectively, at the distal ends thereof, and the elastic sections 113a of the first plier arms 113 are respectively connected with the elastic sections 213a of the second plier arms 213, hence provide similar function described in the first embodiment as distal ends of the first plier arms 113 and the second plier arms 213 being pivoted together, and enable connection and corporate opening and closing between the first plier arms 113 and the second plier arms 213.

Figure 3:
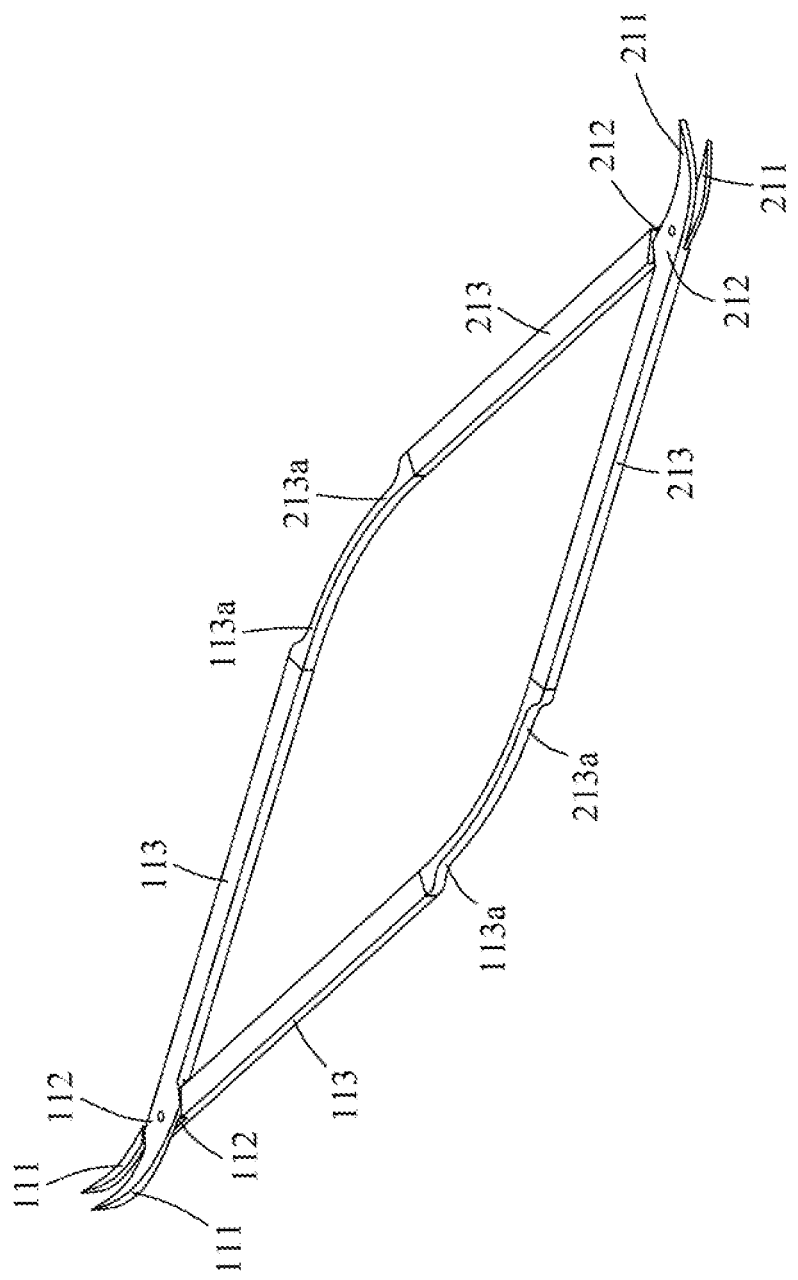
FIG. 3 is a schematic diagram illustrating a third embodiment of the micro needle holder capable of cutting sutures of the present disclosure.

Referring to FIG. 3, a third embodiment of the micro needle holder capable of cutting sutures of the present disclosure is substantially the same as the second embodiment, and differences lies in that, in the third embodiment, the needle holding ends 111 have a curved shape bent in a direction from one end connected to the first shaft connecting parts 112 toward a distal end, and the suture cutting ends 211 have a curved shape bent in a direction from one end connected to the second shaft connecting parts 212 toward a distal end, where the bending is less obvious toward the distal ends. With the curved shapes of the needle holding ends 111 and the suture cutting ends 211, application of force during operation may become more convenient, and the curved shapes of the suture cutting ends 211 may further prevent sutures being cut off falling into bodies of recipients of surgeries.

In conclusion, the needle holding ends 111 and the suture cutting ends 211 disposed on opposite sides may enable the user to operate single-handily to select the needle holding ends 111 for holding the needle or select the suture cutting ends 211 for cutting off the suture, the stitching movement and suture cutting movement may be accomplished in one iteration, the inconvenience during procedure of microsurgeries may be reduced, and any possible mishaps while waiting for exchange of tools may be avoided.

However, the descriptions above are merely embodiments of the present disclosure and should not be construed as limitations to the scope of the present disclosure. All simple equivalent variations and modifications according to appended claims and the present disclosure should fall within the scope of the appended claims.

What is claimed is:

1. A micro needle holder capable of cutting sutures, configured for holding needles and cutting sutures during microsurgeries, comprising:

a needle holding unit comprising a pair of first plier bodies and a first shaft, wherein each of the first plier bodies has a needle holding end, a first shaft connecting part in connection with the needle holding end, and a first plier arm in connection with the first shaft connecting part, the pair of first plier bodies are over-stacked via the first shaft connecting parts and in an intersecting configuration, the first shaft is pivoted at the first shaft connecting parts, so that the first shaft connecting parts are rotatably connected relative to each other, the needle holding ends are configured to open and close relative to each other, and the first plier arms are configured to open and close relative to each other; and a suture cutting unit comprising a pair of second plier bodies and a second shaft, wherein each of the second plier bodies has a suture cutting end, a second shaft connecting part in connection with the suture cutting end, and a second plier arm in connection with the second shaft connecting part, the pair of second plier bodies are over-stacked via the second shaft connecting parts and in an intersecting configuration, the second shaft is pivoted at the second shaft connecting parts, so that the second shaft connecting parts are rotatably connected relative to each other, the suture cutting ends are configured to open and close relative to each other, and the second plier arms are configured to open and close relative to each other;

wherein each of the first plier arms comprises a first elastic section at distal ends thereof and each of the second plier arms comprises a second elastic section at distal ends thereof, and the first elastic sections of the first plier arms and the second elastic sections of the second plier arms are connected with each other for the first plier arms and the second plier arms to elastically open and close corporately;

wherein the distal ends of the first plier arms are separated from each other, and the distal ends of the second plier arms are separated from each other.

2. The micro needle holder capable of cutting sutures according to claim 1, wherein at least one of the needle holding unit and the suture cutting unit further comprises an elastic member provided between the first plier arms or the second plier arms, so that the first plier arms and the second plier arms are elastically opened and closed.

3. The micro needle holder capable of cutting sutures according to claim 1, wherein the first plier arms and the second plier arms are made of a material selected from any one of titanium alloy, tantalum alloy, copper alloy, aluminum alloy, magnesium alloy, stainless steel, nickel alloy, and silicone rubber.

4. The micro needle holder capable of cutting sutures according to claim 1, wherein an opening angle between the suture cutting ends is between 5 to 30 degrees.

5. The micro needle holder capable of cutting sutures according to claim 1, wherein the suture cutting ends have a curved shape bent in a direction from one end connected to the second shaft connecting parts toward a proximal end.

6. The micro needle holder capable of cutting sutures according to claim 1, wherein an opening angle between the needle holding ends is between 5 to 30 degrees.

7. The micro needle holder capable of cutting sutures according to claim 1, wherein the needle holding ends have a curved shape bent in a direction from one end connected to the first shaft connecting parts toward a proximal end.

\* \* \* \* \*